US00PP26511P3

(12) United States Plant Patent
Jacobs

(10) Patent No.: US PP26,511 P3
(45) Date of Patent: Mar. 15, 2016

(54) *CHRYSANTHEMUM* PLANT NAMED 'ZANMUPIZZA'

(50) Latin Name: ***Chrysanthemum×morifolium* Ramat.**
Varietal Denomination: Zanmupizza

(71) Applicant: Chrysanthemum Breeders Association Research B.V., Valkenburg ZH (NL)

(72) Inventor: Henricus Cornelius Maria Jacobs, Valkenburg (NL)

(73) Assignee: Chrysanthemum Breeders Association Research B.V., Valkenburg (NL)

( * ) Notice: Subject to any disclaimer, the term of this patent is extended or adjusted under 35 U.S.C. 154(b) by 187 days.

(21) Appl. No.: 13/998,970

(22) Filed: Dec. 30, 2013

(65) Prior Publication Data
US 2015/0189810 P1 Jul. 2, 2015

(51) Int. Cl.
*A01H 5/00* (2006.01)

(52) U.S. Cl.
USPC ..... Plt./287

(58) Field of Classification Search
USPC ..... Plt./287
See application file for complete search history.

*Primary Examiner* — Keith Robinson
(74) *Attorney, Agent, or Firm* — Steptoe & Johnson LLP

(57) ABSTRACT

A *chrysanthemum* plant named 'Zanmupizza' characterized by its medium sized blooms with purple ray florets and prolific branching; natural season flowering date September 9-13 (week 37); blooming for a period of 5 weeks.

3 Drawing Sheets

Botanical designation: *Chrysanthemum×morifolium* Ramat.

Cultivar denomination: 'Zanmupizza'.

BACKGROUND OF THE INVENTION

The present invention relates to a new and distinct cultivar of *chrysanthemum* plant, botanically known as *Chrysanthemum×morifolium* Ramat., commercially known as a garden mum, and hereinafter referred to by the cultivar denomination 'Zanmupizza'. 'Zanmupizza' is a product of a breeding and selection program for outdoor pot mums (garden mums) which had the objective of creating new cultivars with a double type inflorescence, a natural season flower date around week 37, blooming for a period of 5 weeks. 'Zanmupizza' is a seedling resulting from a cross of the female parent id 30608 (not patented) with the male parent id 22173 (not patented). Plants of the new cultivar 'Zanmupizza' differ from plants of its parent in ray floret color. The ray florets of the seedling are purple, while they are red in the female parent and light pink in the male parent.

The new and distinct cultivar was discovered and selected as a flowering plant by Henricus Cornelius Maria Jacobs on a cultivated field in Rijsenhout, The Netherlands in 2008. The first act of asexual production of 'Zanmupizza' was accomplished when vegetative cuttings from the initial selection in 2008 were propagated further in a controlled environment in Rijsenhout, The Netherlands. In summer, about 6-8 days are needed to initiate roots in cuttings of the new plant, after another 5 days rooted plant are formed. The new cultivar has been found to retain its distinctive characteristics through successive propagations.

BRIEF DESCRIPTION OF THE DRAWINGS

The present invention of a new and distinct variety of *chrysanthemum* (of about 16 weeks) is shown in the accompanying drawings, the color being as nearly true as possible with color photographs of this type.

DESCRIPTION OF THE INVENTION

Figure 1:
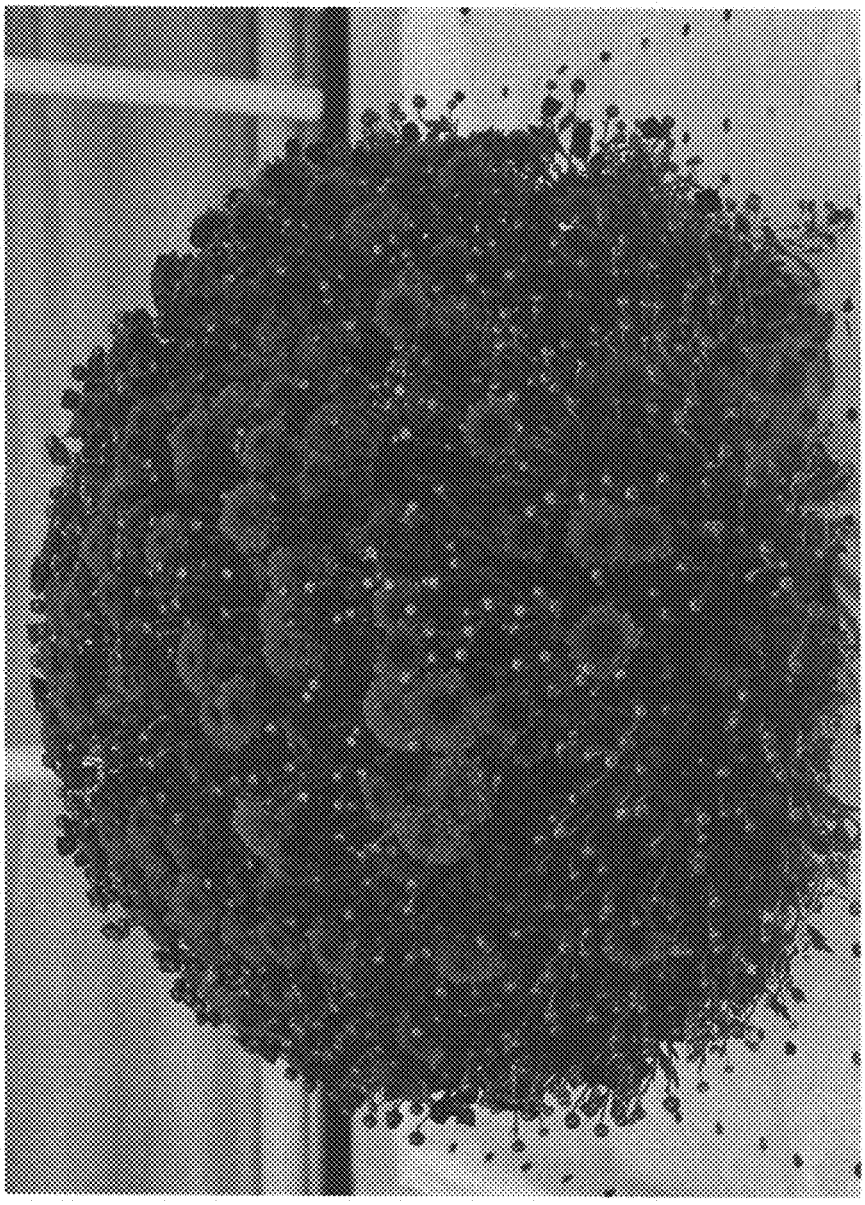
FIG. 1 shows a plant of the cultivar in full bloom.
Figure 2:
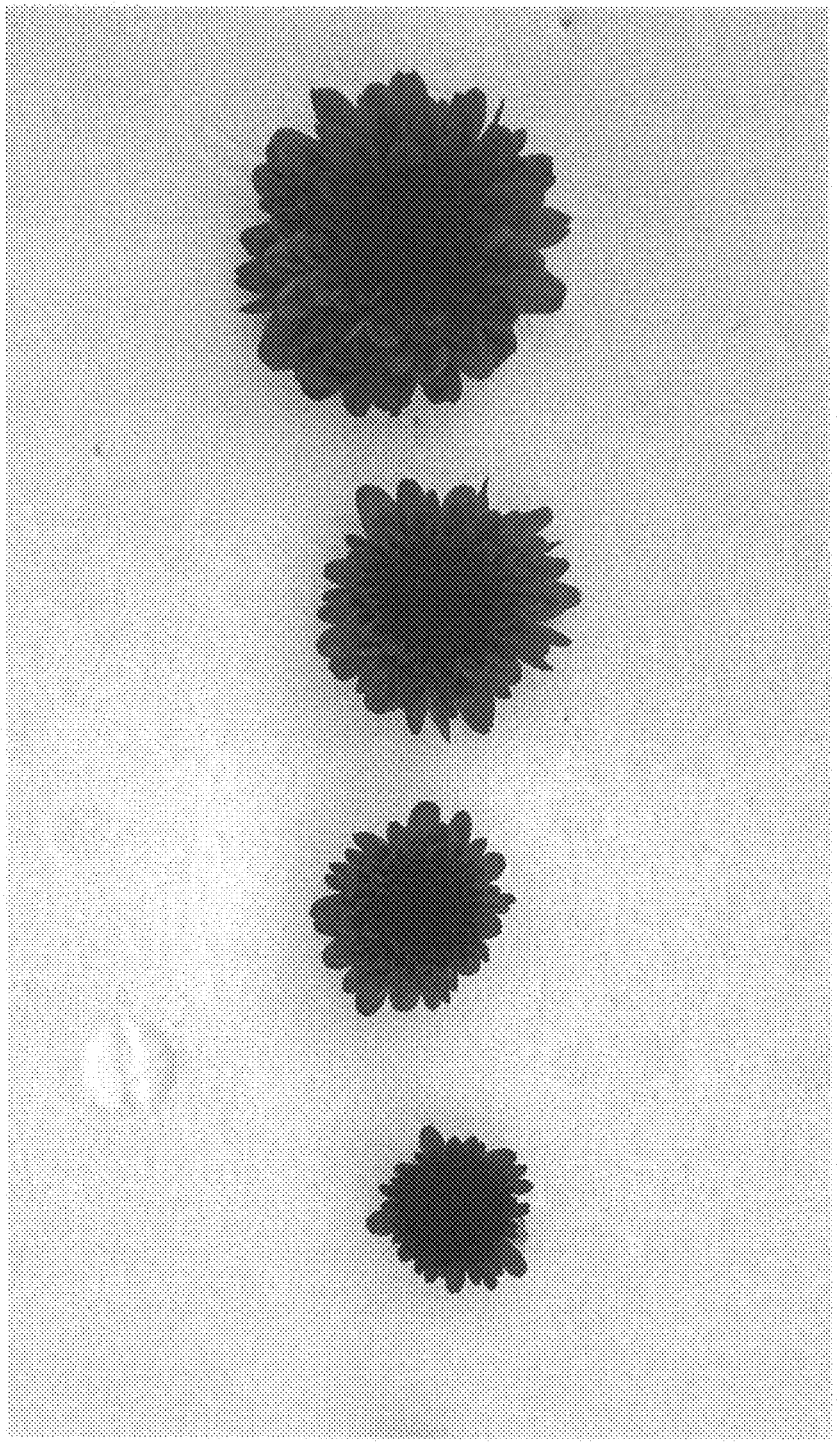
FIG. 2 shows the various stages of bloom of the new cultivar.
Figure 3:
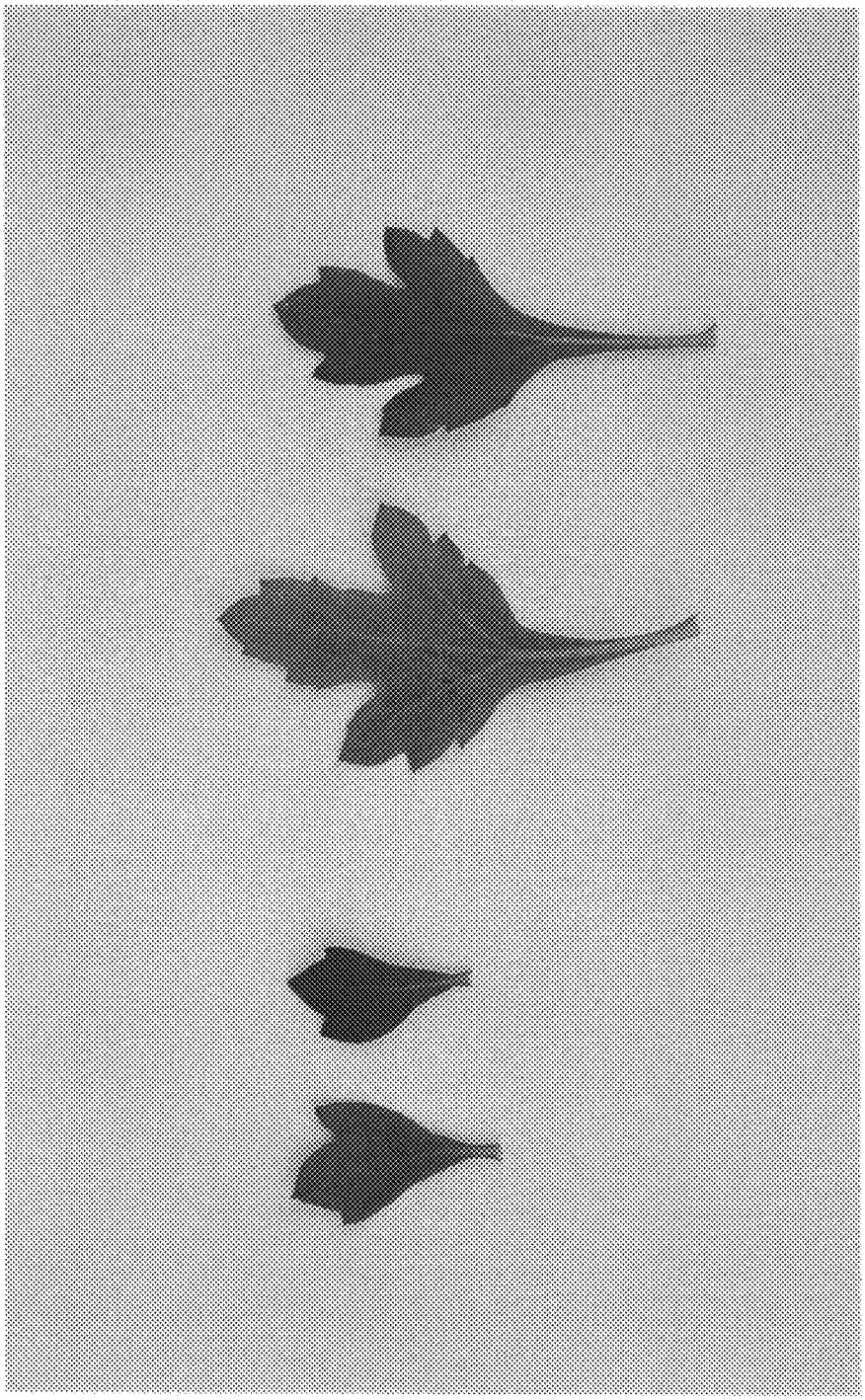
FIG. 3 shows the various stages of foliage of the new cultivar.

The observations and measurements were gathered from plants, in the period of 15 to 22 weeks of age, grown outdoor in Rijsenhout, The Netherlands under natural day length and temperature and planted in week 23 in 2013 (with a warm summer), receiving drip irrigation. The natural blooming date of this crop was September 9-13 (week 37). The average height of the plants was 30 cm. No growth retardants were used. No tests were done on disease or insect resistance or susceptibility. No tests were done on cold or drought tolerance. This new variety produces medium sized blooms with purple ray florets blooming for a period of 5 weeks.

From the cultivars known to the inventor the most similar existing cultivar in comparison to 'Zanmupizza' are 'Venus' (U.S. Plant Pat. No. 14,378) and 'Delphires' (U.S. Plant Pat. No. 12,478). When 'Venus', 'Dephires' and 'Zanmupizza' are being compared the following differences are noticed (1). Natural season flower date. And (2). Inflorescence size. (1). Plants of 'Venus' and 'Delphires' flower earlier in the season than plants of 'Zanmupizza. (2). Inflorescences of 'Venus' and 'Delphires' are larger than those of 'Zanmupizza'.

The following is a description of the plant and characteristics that distinguish 'Zanmupizza' as a new and distinct variety.

The color designations are taken from the plant itself. Accordingly, any discrepancies between the color designations and the colors depicted in the photographs are due to photographic tolerances. The color chart used in this description is: The Royal Horticultural Society Colour Chart, edition 2001.

TABLE 1

Botanical Description of *Chrysanthemum* × *morifolium* Ramat. 'Zanmupizza'

| | |
|---|---|
| **Bud** | |
| Size: | Small; cross-section 7 mm, height 4 mm |
| Shape: | Round |
| Texture: | Pubescent |
| Outside color: | Greyed-green 191A |
| **Phyllaries** | |
| Number: | 21, arranged in 3 rows |
| Shape: | Elliptic |
| Apex: | Acute |
| Base: | Truncate |
| Margin: | Entire |
| Color: | Upper side: Green 141B<br>Lower side: Green 138B |
| Length and width: | 4-5 mm; 2 mm |
| Texture: | Pubescent |
| **Inflorescences** | |
| Type: | Double |
| Height: | 1.8 cm |
| Diameter: | 4.3-4.5 cm |
| Peduncle length: | 8-12 cm |
| Peduncle color: | Green 138C |
| Peduncle diameter: | 1.5-2 mm |
| Peduncle texture: | Pubescent |
| Peduncle strength: | Weak |
| Number per branch: | About. 5 inflorescences |
| Duration of flowering: | 5 weeks |
| Seeds: | Produced in small quantities, ovate, Greyed-brown 199A, length 1.5 mm, diameter 0.5 mm; texture: rough with ribs |
| Fragrance: | Faint *chrysanthemum* odor |
| **Color inflorescences** | |
| Center of inflorescence: | Immature stage: Purple N79A; Mature stage: Purple N79A |
| Color of upper side of ray florets: | Red-purple 72A |
| Color of lower side of ray florets: | Purple N77B |
| Tonality from distance: | A garden mum with purple decorative blooms |
| Color of ray florets after aging of the plant: | Greyed Purple 186A |
| **Ray florets** | |
| Type: | Ligulate |
| Texture: | Upper and lower side smooth |
| Number: | 160-180 |
| Shape: | Elliptic |
| Apex: | Dentate |
| Base: | Attenuate |
| Cross-section: | Flat |
| Longitudinal axis: | Straight |
| Length of corolla tube: | 3 mm |
| Diameter corolla tube: | 1 mm |
| Ray floret margin: | Entire |
| Ray floret length: | 1.5-2.2 cm |
| Ray floret width: | 2-8 mm |
| Ratio length/width: | Medium |
| Disc florets | absent |
| **Receptacle** | |
| Color: | Yellow-green 145D |
| Shape: | Conical raised |
| Height: | 4 mm |
| Diameter: | 3 mm |
| **Reproductive Organs** | |
| Androecium: | Absent |
| Pollen: | Absent |
| Gynoecium: | Present on ray florets |
| Style color: | Yellow-green 154C |

TABLE 1-continued

Botanical Description of *Chrysanthemum* × *morifolium* Ramat. 'Zanmupizza'

| | |
|---|---|
| Style length: | 4 mm |
| Stigma color: | Yellow 7A |
| Stigma width: | 1 mm |
| Ovary: | Enclosed in calyx; color: Yellow-green 149D |
| **Plant** | |
| Type: | Bushy |
| Growth habit: | Spherical shape |
| Growth rate: | Medium |
| Height: | 30 cm |
| Width: | 50 cm |
| Stem color: | Greyed-brown 199A |
| Stem strength: | Strong |
| Stem brittleness: | Not brittle |
| Stem anthocyanin coloration: | present, streaks of Greyed-red 178B |
| Internode length: | 1-2.5 cm |
| Length of lateral branch: | From top to bottom 20-22.cm |
| Lateral branch color: | Green 137 C |
| Lateral branch, attachment: | Strong |
| Lateral branch diameter: | 3 mm |
| Lateral branch texture: | Pubescent with ribs |
| Branching (average number of lateral branches): | Dense, with 8 breaks after pinching |
| Natural season blooming date: | Sep. 9-13 (week 37) in Rijsenhout, The Netherlands |
| Roots-habits: | Freely branching, fine |
| Roots-color: | White 155D |
| **Foliage** | |
| Glossiness: | Leaf upper side: very weak<br>Leaf lower side: very weak |
| Leaf color: | Upper side: Green 139 A-B<br>Lower side: Green 138A |
| Color midvein: | Upper side: Yellow-green 147D<br>Lower side: Yellow-green 148D |
| Size: | Small; length 3-5 cm, width 1.4-2 cm |
| Quantity (number per lateral branches): | 20-22 |
| Shape: | Elliptic |
| Texture upper side: | Sparsely pubescent |
| Texture under side: | Pubescent |
| Venation arrangement: | Palmate |
| Shape of margin: | Serrated |
| Shape of base of sinus between lateral lobes: | Rounded |
| Margin of sinus between lateral lobes: | Diverging |
| Shape of base: | Acute |
| Apex: | Mucronulate |
| Petiole attitude: | Moderately upwards |
| Petiole length: | 1-4 cm |
| Petiole diameter: | 15-25 mm |
| Petiole color: | Yellow-green 147D |
| Stipule: | Small, about 1 mm |

TABLE 2

Differences with the comparison varieties, when grown under identical conditions

| | 'Zanmumipizza' | 'Venus' | 'Delphires' |
|---|---|---|---|
| Natural season flowering date | week 37 | week 35 | week 35 |
| Inflorescence size | 4.3-4.5 cm | 5-5.5 cm | 4.5-5.5 cm |

I claim:

1. A new and distinct *chrysanthemum* plant named 'Zanmupizza' as described and illustrated.

* * * * *